(12) United States Patent
Meskens

(10) Patent No.: US 9,155,900 B2
(45) Date of Patent: Oct. 13, 2015

(54) MEDICAL DEVICE BATTERY CHARGING SYSTEM AND METHODS

(71) Applicant: Werner Meskens, Macquarie University (AU)

(72) Inventor: Werner Meskens, Macquarie University (AU)

(73) Assignee: COCHLEAR LIMITED, Macquarie University (AU)

( * ) Notice: Subject to any disclaimer, the term of this patent is extended or adjusted under 35 U.S.C. 154(b) by 224 days.

(21) Appl. No.: 13/922,856

(22) Filed: Jun. 20, 2013

(65) Prior Publication Data

US 2014/0379047 A1     Dec. 25, 2014

(51) Int. Cl.
| | |
|---|---|
| G08B 21/00 | (2006.01) |
| A61N 1/378 | (2006.01) |
| A61N 1/36 | (2006.01) |
| H02J 5/00 | (2006.01) |
| H02J 7/00 | (2006.01) |
| H02J 7/02 | (2006.01) |

(52) U.S. Cl.
CPC .......... *A61N 1/3787* (2013.01); *A61N 1/36032* (2013.01); *H02J 5/005* (2013.01); *H02J 7/0004* (2013.01); *H02J 7/0027* (2013.01); *H02J 7/025* (2013.01)

(58) Field of Classification Search
None
See application file for complete search history.

(56) References Cited

U.S. PATENT DOCUMENTS

| | | | |
|---|---|---|---|
| 4,352,960 A | 10/1982 | Dormer et al. | |
| 5,949,895 A | 9/1999 | Ball et al. | |
| 6,560,488 B1 | 5/2003 | Crawford | |
| 7,177,690 B2 | 2/2007 | Woods et al. | |
| 7,266,209 B1 | 9/2007 | House | |
| 7,571,006 B2 | 8/2009 | Gordon et al. | |
| 7,599,508 B1 | 10/2009 | Lynch et al. | |
| 7,818,066 B1 | 10/2010 | Palmer | |
| 2007/0182367 A1* | 8/2007 | Partovi | 320/108 |
| 2007/0208403 A1 | 9/2007 | Della Santina et al. | |
| 2007/0279002 A1* | 12/2007 | Partovi | 320/115 |
| 2009/0096413 A1* | 4/2009 | Partovi et al. | 320/108 |
| 2009/0212736 A1* | 8/2009 | Baarman et al. | 320/106 |
| 2010/0046778 A1 | 2/2010 | Crawford et al. | |
| 2010/0046779 A1 | 2/2010 | Crawford et al. | |
| 2010/0060232 A1 | 3/2010 | Boyles et al. | |
| 2010/0295372 A1 | 11/2010 | Hyde et al. | |
| 2012/0150259 A1* | 6/2012 | Meskens | 607/57 |
| 2012/0189146 A1 | 7/2012 | Wuidart | |

(Continued)

FOREIGN PATENT DOCUMENTS

| | | |
|---|---|---|
| JP | 2009021910 A | 1/2009 |
| KR | 2008084112 | 9/2008 |

(Continued)

OTHER PUBLICATIONS

PCT International Search Report and Written Opinion in International Application PCT/IB2014/001965, mailed Jan. 26, 2015, 14 pgs.

(Continued)

*Primary Examiner* — Travis Hunnings

(57) ABSTRACT

Systems, methods, and apparatuses may be used to charge battery-powered devices using a charging device. Such battery-powered devices include the external portions of auditory prostheses or other medical devices. The charging device prioritizes the charging requirements of a number of batteries and transfers power to one or more batteries. The charging device also sends a signal to activate an indicator on each external portion.

30 Claims, 12 Drawing Sheets

(56) References Cited

U.S. PATENT DOCUMENTS

2012/0214418 A1* 8/2012 Lee et al. .................. 455/41.2
2013/0182874 A1* 7/2013 Buehlmann ................ 381/312

FOREIGN PATENT DOCUMENTS

| KR | 1020120085980 A | 8/2012 |
| WO | WO 2007/146773 | 12/2007 |
| WO | WO 2009/056167 | 5/2009 |
| WO | WO 2010/017118 | 2/2010 |
| WO | WO 2010/056768 | 5/2010 |

OTHER PUBLICATIONS

Datasheetoo, "Wireless Battery Charger Chip Circuit Design", posted by admindata on Dec. 24, 2009, found online at: http://datasheetoo.com/wireless/wireless-battery-charger-chip-circuit-design.html, 2 pgs.

* cited by examiner

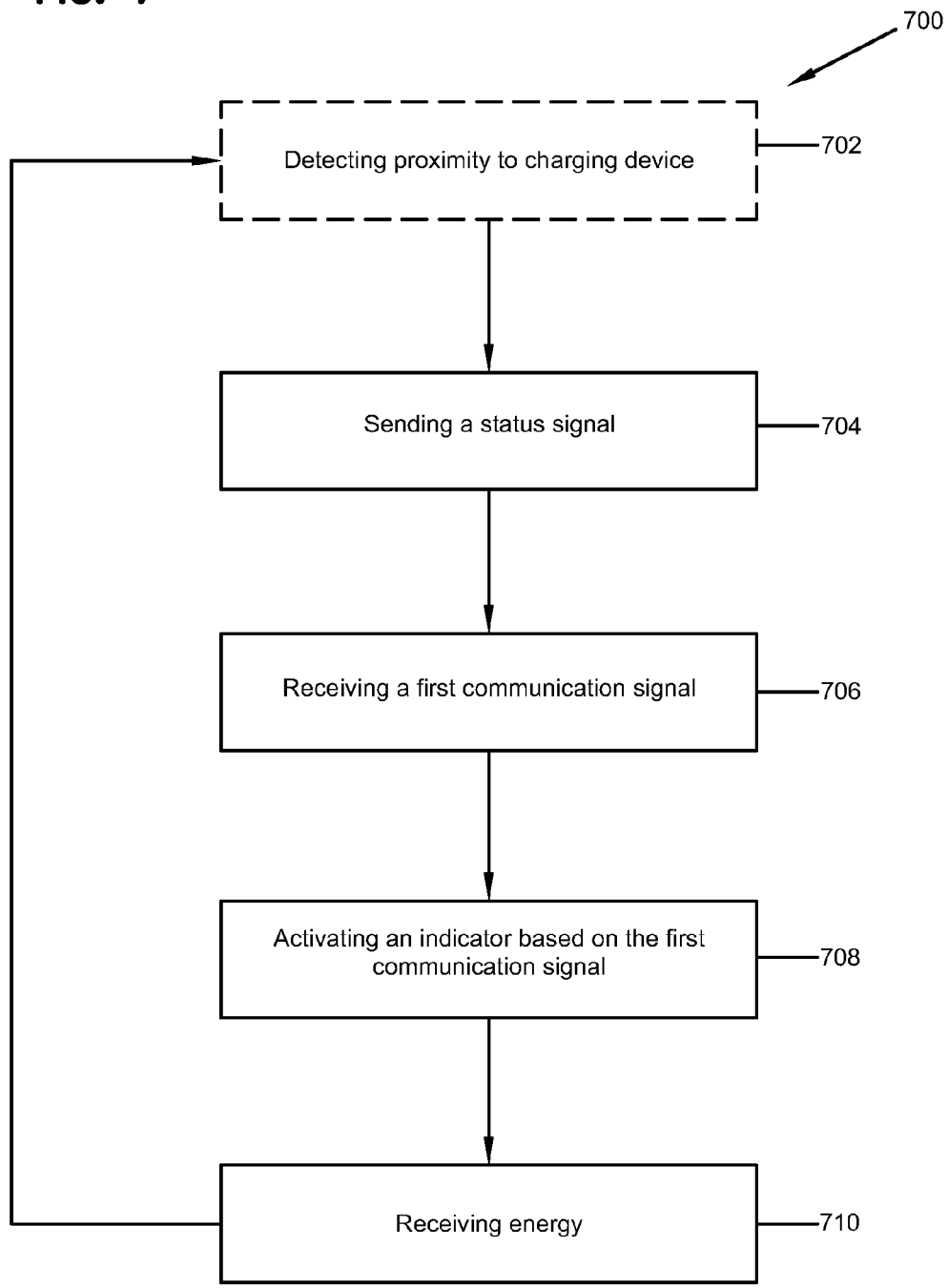

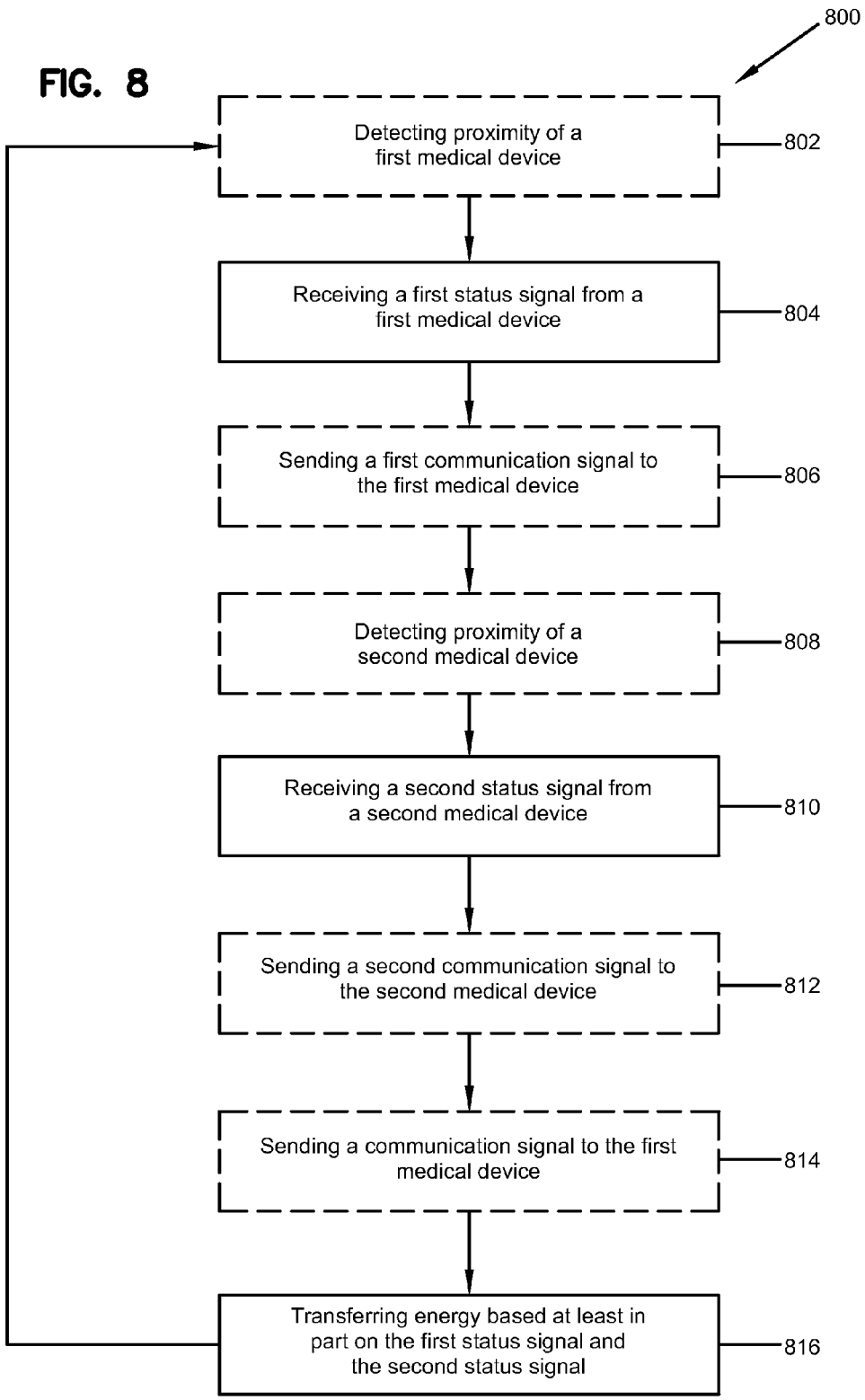

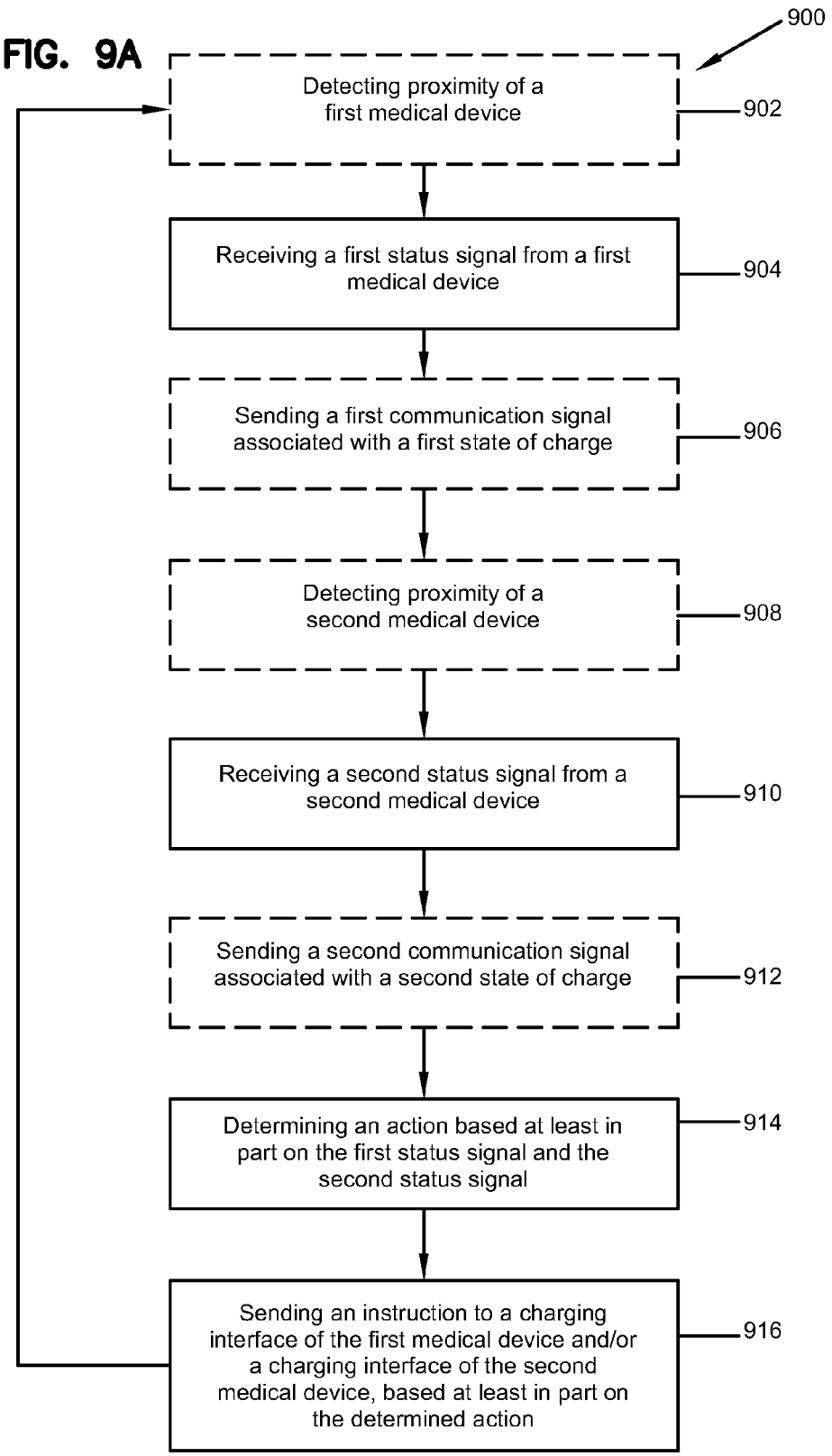

MEDICAL DEVICE BATTERY CHARGING SYSTEM AND METHODS

BACKGROUND

Auditory prostheses, such as cochlear implants, include an implantable portion having a stimulating assembly and an external portion having speech processing hardware and software, as well as a battery. The battery provides power to the external portion so as to enable the appropriate signals to be sent to the implantable portion. As the battery discharges, it becomes necessary for a recipient to trade an external portion having little or no remaining power for an external portion having more power. Thus, it is desirable to have multiple external portions available to a prosthesis recipient, so a sufficient power supply is constantly available.

SUMMARY

Embodiments disclosed herein relate to systems, methods, and apparatuses that are used to prioritize the charging of, and charge, the batteries of medical devices. Those devices include, for example, cochlear implants or other hearing aids or devices. A charging device receives one or more external portions of the medical device. The status of each battery in each medical device, as well as other information, is communicated to the charging device. The charging device then prioritizes the charging of the batteries of the various external portions. Additionally, the charging portion can signal a particular external portion to display information regarding, for example, its state of charge.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

FIG. 7 is a method of communicating with a charging device.

FIG. 8 is a method of charging a battery of a medical device.

FIG. 9A is a method of managing the charging of multiple batteries of a medical device.

DETAILED DESCRIPTION

Figure 1:
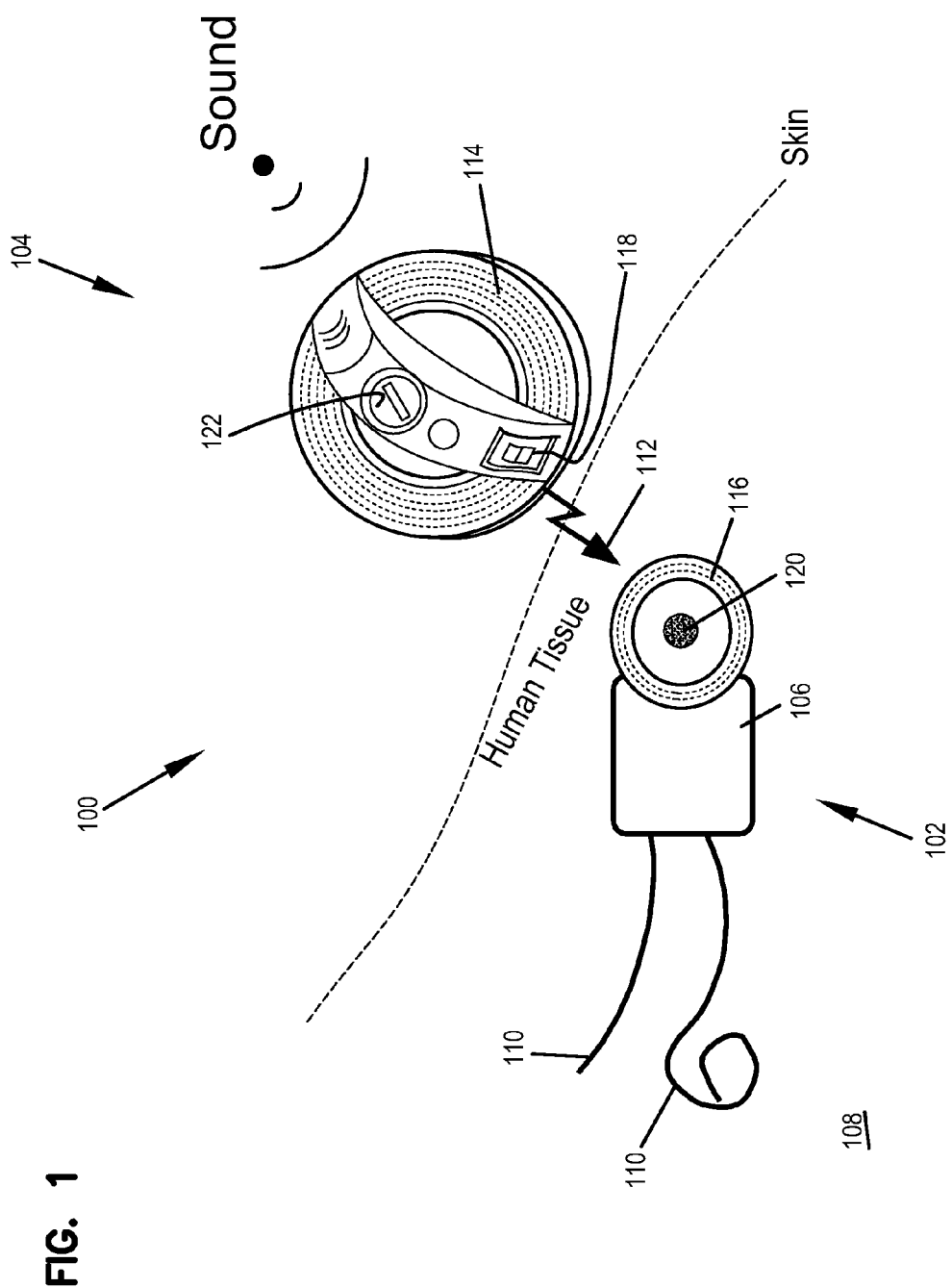
FIG. 1 is a schematic perspective view of an embodiment of an auditory prosthesis, including an implantable portion and an external portion.

While the technologies disclosed herein have particular application in the cochlear implant devices depicted in FIG. 1, it will be appreciated that the systems, methods, and apparatuses disclosed can be employed to charge the batteries of other types of hearing prostheses. For example, the embodiments disclosed herein can be used to charge the batteries of traditional hearing aids, hearing prostheses, active transcutaneous bone conduction devices, passive transcutaneous devices, middle ear devices, or other devices that include an external battery. Furthermore, the embodiments disclosed herein may be utilized to charge medical devices other than hearing prostheses, where an external battery unit is utilized in conjunction with an implantable device, or where a medical device simply includes a battery. The technologies disclosed herein will be described generally in the context of external portions of medical devices where the external portions contain batteries. Certain aspects of the technology however, for example, the external portions of a cochlear implant identified in FIG. 1, are described in the context of auditory prostheses.

FIG. 1 is a schematic perspective view of an embodiment of an auditory prosthesis 100, in this case, a cochlear implant, including an implantable portion 102 and an external portion 104. The implantable portion 102 of the cochlear implant includes a stimulating assembly 106 implanted in a body (specifically, proximate and within the cochlea 108) to deliver electrical stimulation signals to the auditory nerve cells, thereby bypassing absent or defective hair cells. The electrodes 110 of the stimulating assembly 106 differentially activate auditory neurons that normally encode differential pitches of sound. This stimulating assembly 106 enables the brain to perceive a hearing sensation resembling the natural hearing sensation normally delivered to the auditory nerve.

The external portion 104 includes a speech processor that detects external sound and converts the detected sound into a coded signal 112 through a suitable speech processing strategy. The coded signal 112 is sent to the implanted stimulating assembly 106 via a transcutaneous link. In one embodiment, the signal 112 is sent from a coil 114 located on the external portion 104 to a coil 116 on the implantable portion 102. The stimulating assembly 106 processes the coded signal 112 to generate a series of stimulation sequences which are then applied directly to the auditory nerve via the electrodes 110 positioned within the cochlea 108. The external portion 104 also includes a battery and a status indicator 118, the functionality of which is described below. Permanent magnets 120, 122 are located on the implantable portion 102 and the external portion 104, respectively.

Figure 2:
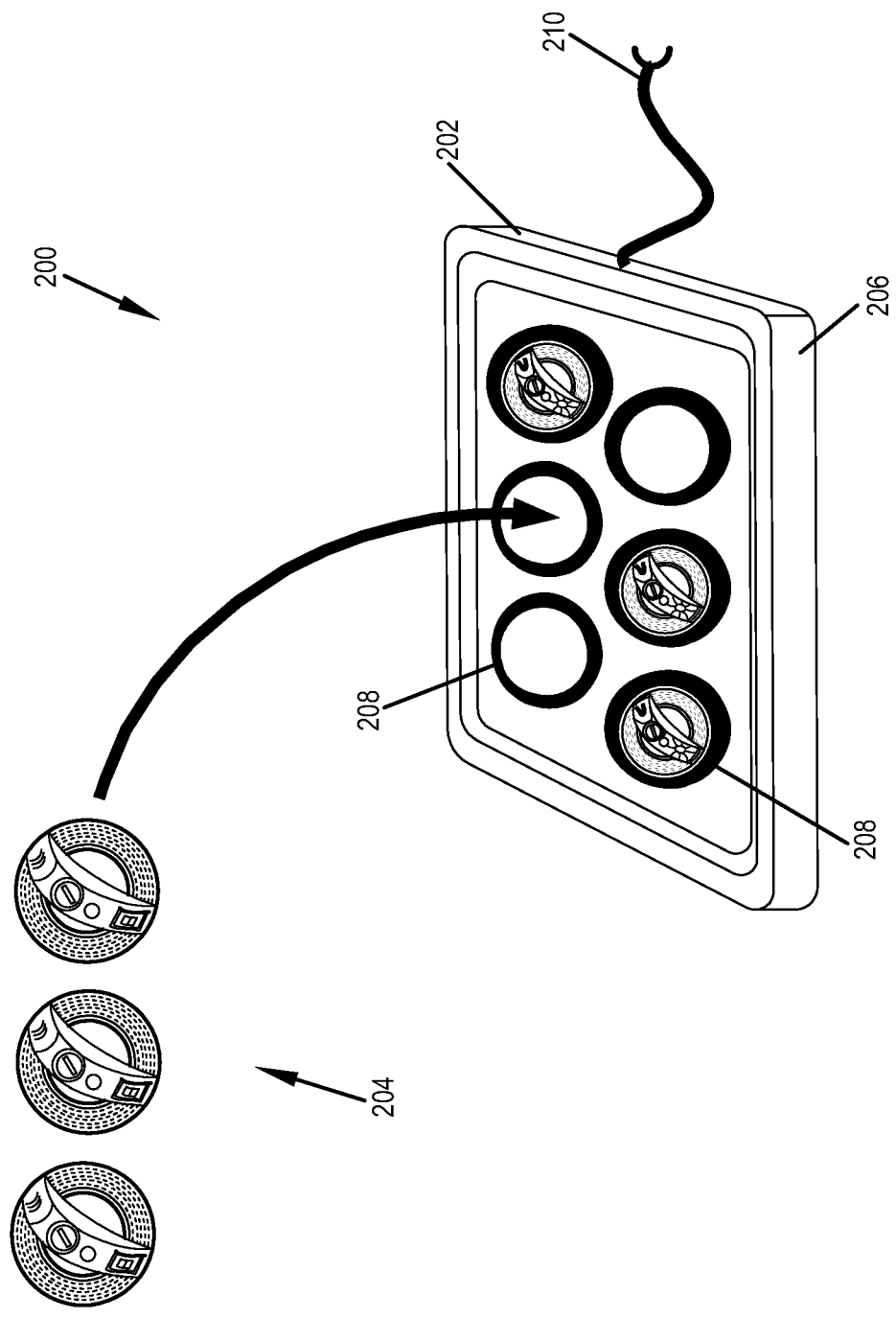
FIG. 2 is a schematic perspective view of an embodiment of a system including a charging device and external portions of an auditory prosthesis.

FIG. 2 is a schematic perspective view of an embodiment of a system 200 including a charging device 202 and multiple external portions 204 of an auditory prosthesis. Such a system 200 is used for recharging of the battery of each external portion 204 via wireless power or energy transfer with the charging device 202 (e.g., over inductive coupling). This charging occurs over the same coil that provides power and data to the implantable portion of an auditory prosthesis. The charging device 202 includes a housing 206 and a number of charging interfaces 208 located therein. In the depicted embodiment, the interface 208 locations are defined by circular targets sized to match the external portions 204, which makes it easy for a recipient to understand where to locate the external portions 204 for proper charging. The charging interfaces 208 can have any form factor as required or desired for a particular application. In certain embodiments, the charging interfaces 208 are recessed or raised portions of the housing 202, configured to mate with the external portions 204. Alternatively, the charging station can include multiple plugs that are received in the external portions. In other embodiments, the charging interfaces 208 can be hard connections such as receivers that mate with physical plugs on the external portion 204. In the context of the present disclosure, however, signals and power sent wirelessly between the charging device 202 and external portions 204 will be described. In the present embodiment, the charging intelligence, described in more detail below, is contained within the housing 206 of the charging device 202. Accordingly, the charging device 202 need only be connected to some type of external power source, typically via a plug connection 210. This plug can be connected to a building power service, automobile accessory power jack, a computer (via, e.g., a USB connection), etc.

Figure 3:
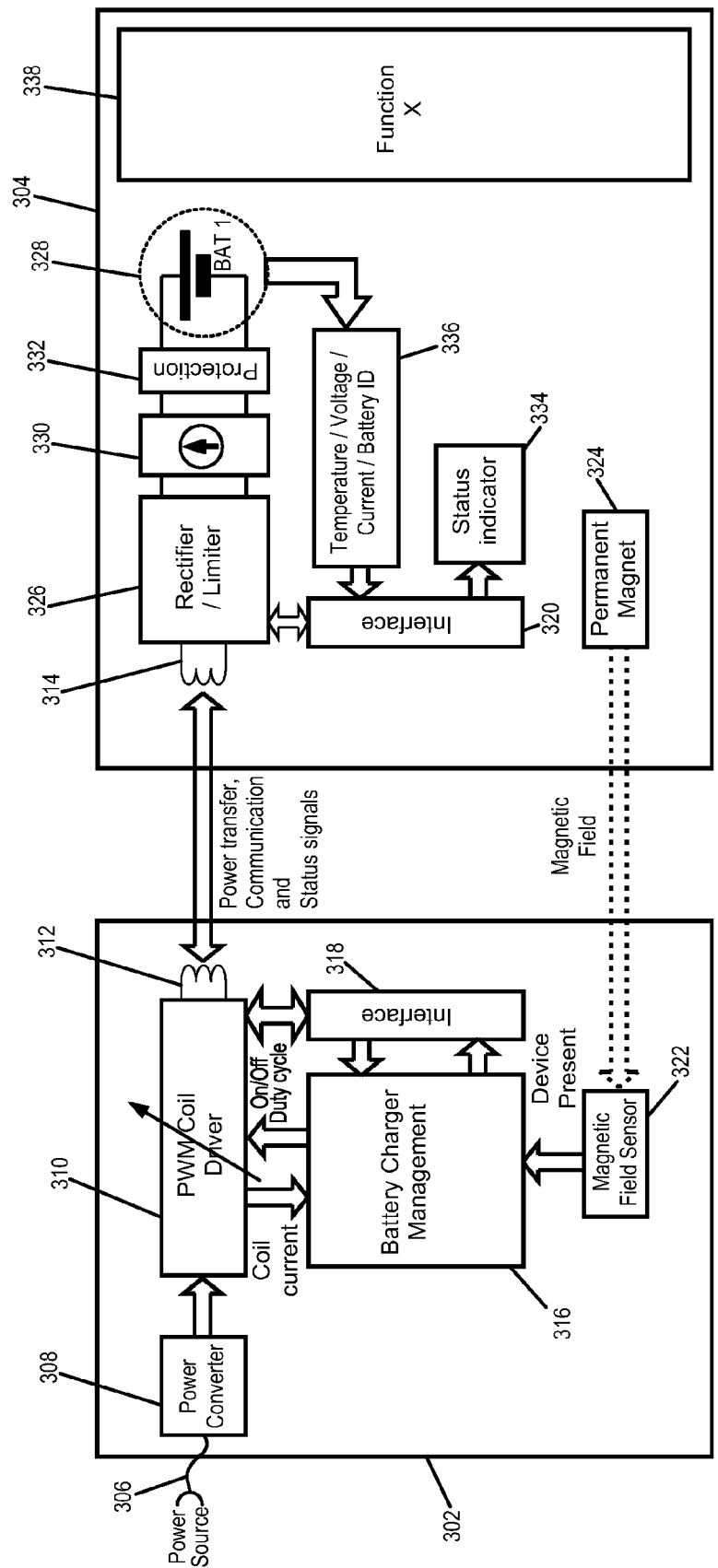
FIG. 3 is an embodiment of a system including a charging device and an external portion of an auditory prosthesis.

FIG. 3 is an example of a system 300, including a charging device 302 and an external portion 304 of an auditory prosthesis. The charging device 302 includes a power plug 306 to an external power source and a power converter 308 for converting the external power to be utilized by the charging device 302. The interface 320 can be hardware, software, or a combination of hardware and software that receives the communication signal and actuates the indicator 334. In the depicted embodiment, the interface 320 is hardware. A pulse width modulation (PWM) coil driver 310 sends a signal to an associated coil 312, which transfers power or energy to an associated coil 314 on the external portion 304. In this embodiment, power, communication signals, and status signals are transferred wirelessly (e.g., at about 13.56 MHz AC) over the closely-coupled coils 312, 314. A battery charger management subsystem 316 contains the charging intelligence described further herein and controls the power transfer sent from the charging device 302. Communication signals are sent from a charging device interface 318 to an associated interface 320 on the external portion 304, via the coils 312, 314. Alternatively, the communication signals can be generated and sent directly from the battery charger management subsystem 316. In this example, a magnetic field sensor 322 is utilized to detect the magnetic field generated by the permanent magnet 324 located on the external portion 304. Thus, proximity between the charging device 302 and external portion 304 is detected and the charging device 302 sends a communication signal that invokes a status request of the external portion 304 by means of a pulsating or modulated charging signal.

The external portion 304 sends its status signal to the charging device 302 by using backlink telemetry pulses or load modulation. The status signal can include the battery identification and authentication information, as well as type of the battery, battery charging history, temperature, and the like. Subsequently, a communication signal is transferred by means of a pulsating or modulated charging signal. The communication signal received by the interface 320 can send a signal to activate a status indicator 334 located on the external portion 304. The status indicator 334 is generally associated with a state of charge of the battery 328. A rectifier 326 converts the AC current to a DC current to charge an onboard battery 328. After rectification, the current source 330 provides a constant current charge, followed typically by a constant voltage charge cycle (e.g., about 4.1 V for a Li-ion battery). Protection element 332 includes one or more of over-voltage, over-current, and over-temperature protection devices for protection of the battery 328 during current sinking and sourcing. The battery status module 336 delivers information about the battery 328 to the battery charger management subsystem 316. Speech processing and other functions are contained within the operating subsystem 336 and are not described further herein.

Figure 4:
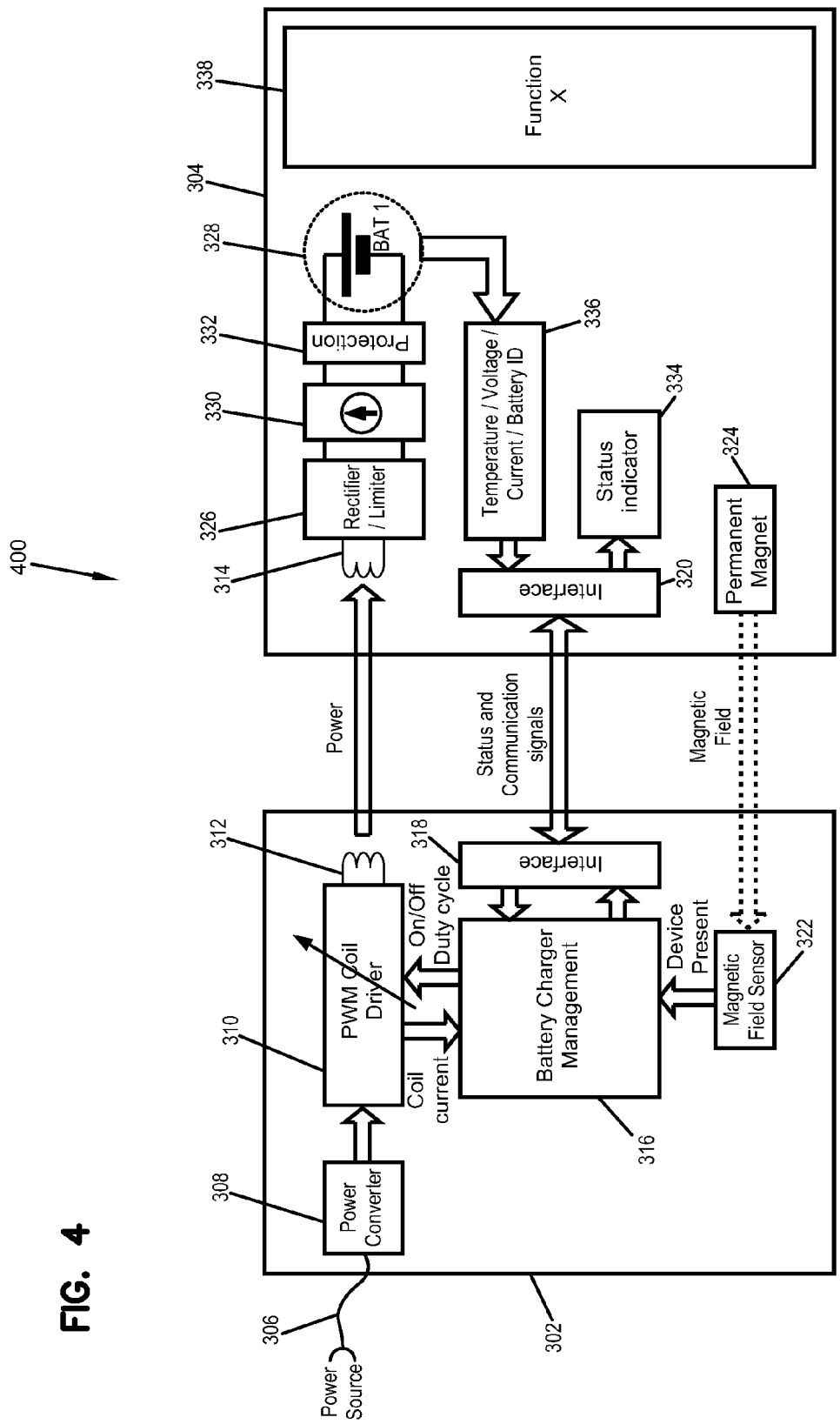
FIG. 4 is another embodiment of a system including a charging device and an external portion of an auditory prosthesis.

FIG. 4 depicts another embodiment of a system 400 that includes all the components depicted in FIG. 3. Here the system 400 sends status and communication signals directly between the two interfaces 318, 320. Thus, the status and communication signals are sent over a bi-directional link separate from the transferred power, which is uni-directional and limited to energy transfer only. The status signal sent can include battery temperature, power remaining, voltage, current, battery identification information, etc. This information is utilized by the battery charger management module 316 to optimize battery charging procedures, identify the battery 328 (and, therefore, the external portion 304), calculate efficiency of the battery based on the change in voltage levels recorded over time, etc.

Figure 5:
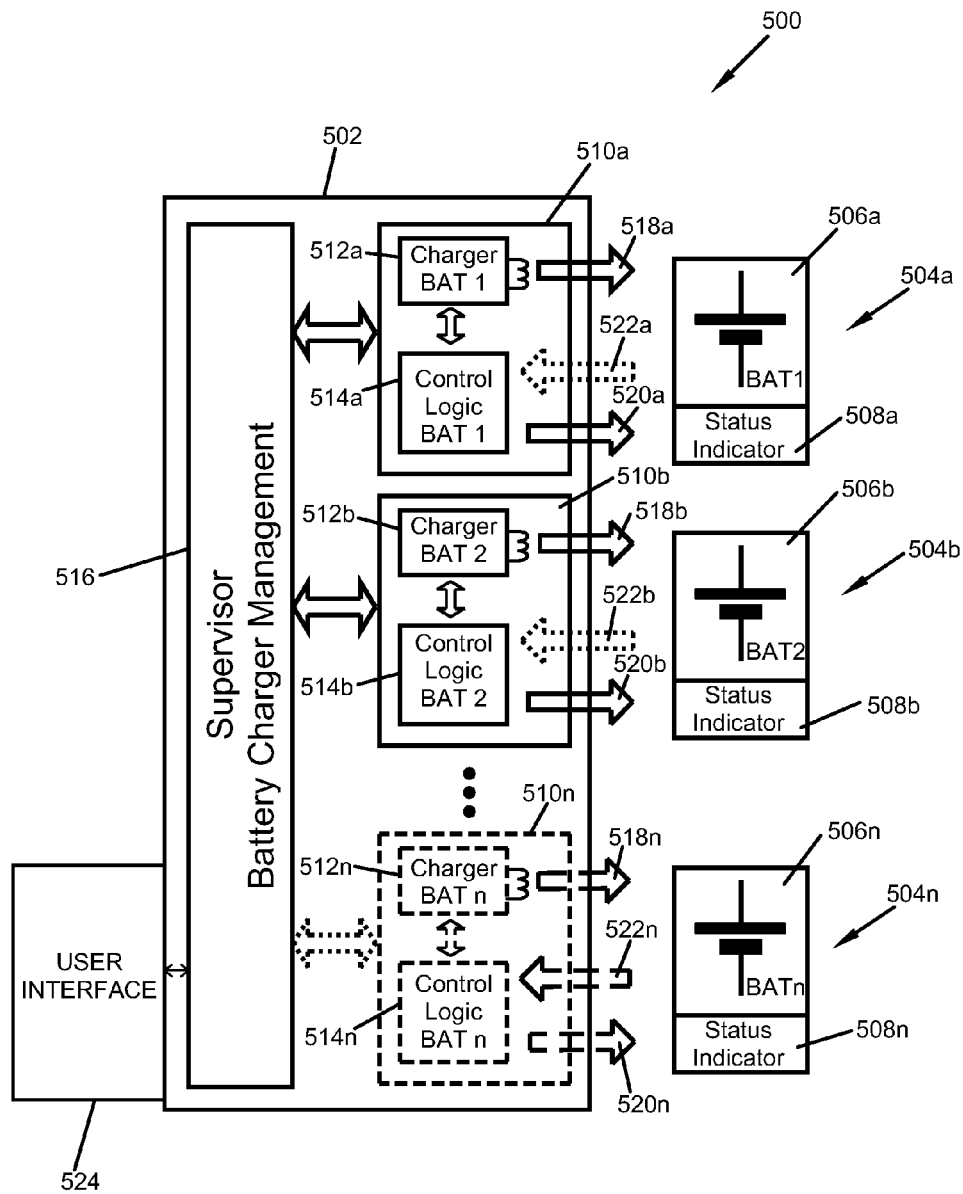
FIG. 5 is an embodiment of a battery charger management subsystem of a charging device and external portions of an auditory prosthesis.

The technologies described herein have application in systems that utilize a single charging device to charge multiple external portions of an auditory prosthesis. FIG. 5 depicts an example of such a system 500. The elements depicted therein can be incorporated into the basic charging systems 300, 400 of FIGS. 3 and 4. The depicted system 500 includes a charging device 502 and a plurality of external portions 504 of an auditory prosthesis. Each external portion 504 includes a battery 506, a status indicator 508, and other components, such as those depicted above. Each external portion 504 is received on the charging device 502 at a charging interface 510. It should be noted that that a particular external portion 504 need not be associated with a particular charging interface 510. That is, external device 504a can be received on any charging interface 510, not specifically the depicted charging interface 510a. Each charging interface 510 includes a charging module 512, for example, the PWM coil driver and coil described above. Each interface 510 also includes a control module 514, which is used to communicate with the associated external portion 504, as described above. Each charging interface 510 communicates directly with a battery charger management module 516, which includes all the internal logic and intelligence to initiate, manage, and prioritize charging of the batteries 506 of the various devices 504. In an alternative embodiment, the control modules 514 can be eliminated and the battery charger management module 516 communicates directly with each external portion 504, controls the transfer of energy, etc. However, manufacturability and maintenance of the charging device 502 may be improved by including discrete control modules 514 at each charging interface 510.

Signals sent between the charging device 502 and the external portions 504 are as described above, and include a communication signal 520. Additionally, power or energy 518 is sent from the charging device 502. In this embodiment, a status signal 522 is sent from the external portion 504 to the charging device 502. A predetermined interaction sequence can dictate the type of information sent between the charging device 502 and the external portions 504. For example, the charging device 502 can first request or command that particular information to be sent from the external portion 504. In response or reply, the external portion 504 may send the requested information in the status signal 522. The various signals sent between the charging device 502 and external portions 504 allow the battery charger management module 516 to initiate, manage, and prioritize charging of the batteries 506. Operation of the battery charger management module 516 is described below.

A user interface 524 (in the form of a keyboard, graphic user interface (GUI), or other implement), can be utilized by the recipient to provide additional instructions or preferences to the charging device 502. These may include instructions to ignore selected external portions 504, ensure one external portion 504 is always at maximum charge, quick charge the most depleted battery 506 disable a particular charging interface 510, etc.

Figure 6C:
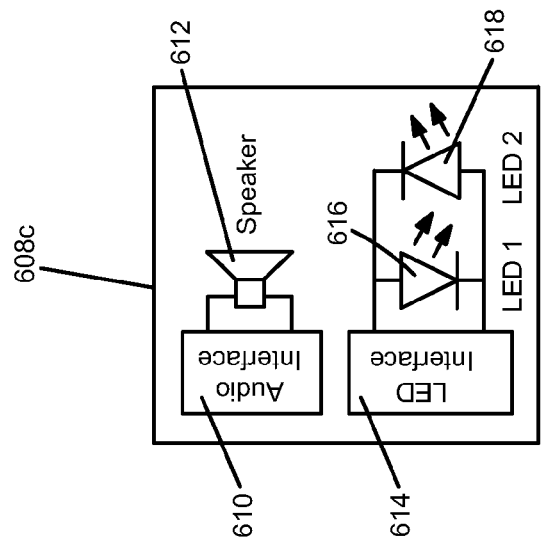
FIG. 6C is an embodiment of a status indicator for an external portion of an auditory prosthesis.
Figure 6B:
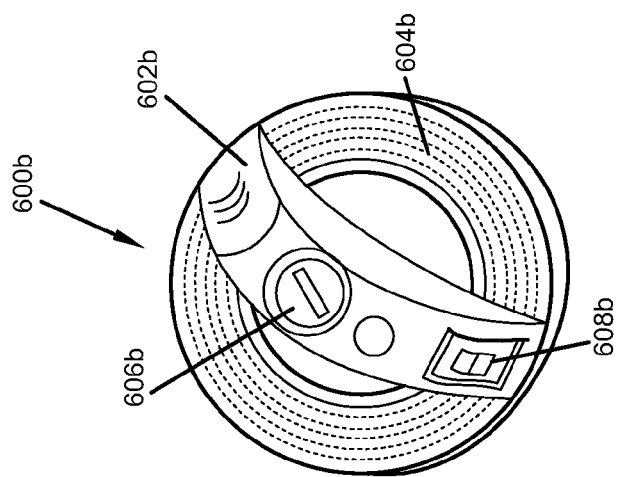
FIGS. 6A and 6B are schematic perspective views of embodiments of external portions of an auditory prosthesis.
Figure 6A:
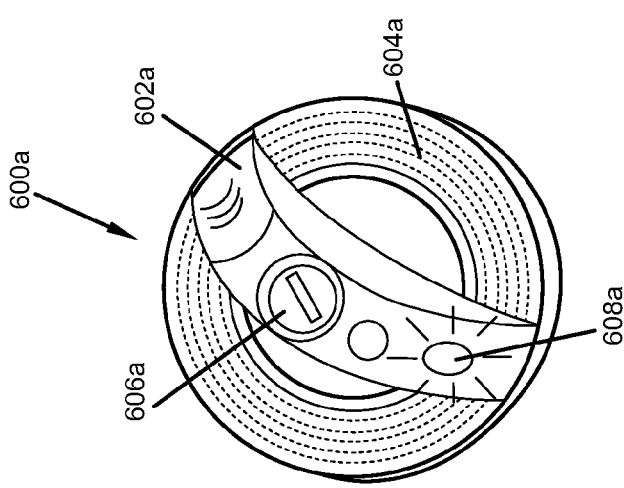

FIGS. 6A and 6B depict two embodiments of external portions 600 of a medical device, in this case, an auditory prosthesis. Each external portion 600 includes a body 602 and a coil 604 connected thereto. The body 602 can include a permanent magnet 606 as described above. Various types of indicators 608 are depicted in FIGS. 6A and 6B. In the external portion 600a, the indicator 608a is a light emitting diode (LED). The LED is activated based on a communication signal sent from a charging device, as described herein. In certain embodiments, the LED emits a single color and can illuminate during charging, once a battery is completely charged, or based on some other status condition, as required or desired for a particular application. In the external portion 600b, the indicator 608b is a display. In certain embodiments, the display is a liquid crystal display (LCD) or other type of display that can present information in alphanumeric, graphic, bitmapped, or other formats. Information presented can include a graphical image of a battery to indicate charge level, an alphanumeric image indicative of hours of charge remaining, or other information.

FIG. 6C depicts another example of a status indicator 608c that includes multiple indicator components. Here, the status indicator 608c includes an audio interface 610 that is coupled to a speaker 612 for emitting sounds indicative of battery charge level, battery status, error conditions, etc. Alternatively or additionally, a buzzer, piezoelectric vibrating element, or other sound-producing element can be utilized. An LED interface 614 activates one or more LEDs 616, 618. Multiple LEDs 616, 618, each emitting a different color, can be utilized to depict various conditions of an external portion battery or the external portion itself, such as battery charge level, battery status, error conditions, etc. Alternatively, a single LED can be utilized. Differences in indication states (that is, in the case of LED emissions, steady emission, flashing, smooth fading, stepping down or up, etc.) can be utilized in certain embodiments to communicate the desired information to a recipient. The information displayed by the status indicators on the various external portions allow a user to determine which external portion to use in conjunction with their medical device. Additionally, the information displayed can allow a user to determine which external portion requires service, replacement, and/or disposal.

FIG. 7 is a method 700 of communicating with a charging device, by a medical device that includes a battery. The method 700 begins once the medical device is placed in close enough proximity to the charging device, such that signals (communication, status, power, etc.) may be sent between the devices (operation 702). In the method 700, the medical device can detect the proximity, by any or all of a combination of a physical connections, radio-frequency identification (RFID) signal, magnetic field detection, etc. A discrete operation of detecting proximity is entirely optional. The method 700 continues with the medical device sending a status signal to the charging device (operation 704). The status signal can be sent once proximity is detected or as the result of a query from the charging device. In another embodiment, the status signal is contained within the signal that establishes proximity. That is, the status signal may be the RFID signal associated with proximity sensing. In certain embodiments, the status signal includes the level of charge of the battery, battery history, depicted as a function of voltage and/or current, as a percentage of total charge available, amount of battery life remaining, a voltage measurement, an error condition, etc. In other embodiments, the status signal can include a temperature of the battery, current, battery identification information, etc. Status signals including combinations of such information are also contemplated. In other embodiments, status signals need only include information particularly requested by a charging device. In response to the status signal, the charging device sends a communication signal that is received by the medical device (operation 706). The communication signal is typically associated with a state of charge of the battery and the additional instructions or preferences provided by the recipient to the charging device. Upon receipt of the communication signal, the medical device can optionally activate an indicator located thereon (operation 708), based on the information sent in the first communication signal. Thus, at the command of the charging device, the medical device provides visual and/or audible information to the recipient about the condition of that particular medical device. This allows the recipient to make a determination as to whether to use that device again, or take other actions. By activating an indicator on the medical device (as opposed to one located on the charging device), recipient confusion can be reduced or eliminated.

Last, the medical device receives energy or power (operation 710). Most commonly, the energy received increases or maintains the level of charge of the battery. In certain embodiments, however, the energy can be in the form of a reverse flow of energy (that is, energy is discharged from the battery). Thus, energy transferred may be in the form of, for example, a trickle charge, a normal charge, a fast charge, an end of charge, and a forced discharge. The trickle charge delivers sufficient power to maintain the battery power at or near its present charge state. The normal charge and fast charge both charge the battery, and are distinguished largely based on rate of charge. The end of charge terminates charging of the battery. The forced discharge drains the battery, which is advantageous for certain types of batteries to ensure proper operation and long battery life. In certain embodiments, batteries having a charge level at or near a low predetermined threshold are forcibly discharged prior to the charging process beginning. The method 700 can be repeated as long as the medical device is proximate the charging device, with the device updating the charging device about the battery status, the medical device receiving different rates of energy transfer from the charging device, etc. This updating can occur at predetermined time intervals.

FIG. 8 is a method 800 of charging a battery of a medical device. Similar to the method 700 above, a first medical device to be charged is first (optionally) detected in proximity to a charging device (operation 802). Thereafter, the method 800 continues when the charging device (more specifically, a battery charger management module or a control module) receives a status signal from the first medical device (operation 804). Examples of the type of information received in the status signal are described above. Thereafter, the charging device optionally sends a first communication signal to the first medical device (operation 806). As described above, the first communication signal is associated with a first state of charge of the battery of the medical device (determined from the status signal), and ultimately instructs the medical device to activate the indicator located thereon.

In a charging device having more than one charging station, such as those depicted in FIGS. 2 and 5, additional medical devices can also be optionally detected in proximity with the charging device (operation 808). As with the first medical device, a second status signal is received from the second medical device (operation 810). A second communication signal associated with a second state of charge of the second battery is optionally sent to the second medical device (operation 812), ultimately instructing the second medical device to activate the indicator located thereon. Due to the presence of the second medical device the battery charger manager can decide to send a communication signal (operation 814) to the first medical device if an update is required. Although described in the context of a second medical device, operations 808 through 814 can be repeated for any number of medical devices placed in proximity to the charging device. The charging device then transfers power to the battery of the first and/or second medical device. This transfer of power can be based at least in part on the first status signal and the second status signal (operation 816). In alternative embodiments, power can be transferred to all medical devices simultaneously, though this may increase the temperature of the charging device, power requirements, or change other conditions which may not be desirable. As with the method 700 above, the various operations may be repeated as the various batteries are charged and discharged, additional medical devices are placed in proximity with or removed from the charging device, etc.

FIG. 9A depicts a method 900 of managing the charging of multiple batteries, typically those used in conjunction with a medical device. Similar to the methods described above, a first medical device to be charged is placed in proximity to a charging device and optionally detected (operation 902). Thereafter, the charging device receives a first status signal from the first medical device (operation 904). The charging device sends an optional first communication signal to the medical device (operation 906). The first communication signal can include an instruction for the first medical device to activate an indicator. In systems where multiple medical devices are charged, additional medical devices may also be placed in proximity with the charging device and optionally detected (operation 908). As with the first medical device, a second status signal is received from the second medical device (operation 910). The charging device sends a communication and charging signal to all the medical devices in proximity (operation 908). The communication signal can include an instruction for each associated medical device to activate an indicator. A second communication signal associated with a second state of charge of the second battery is optionally sent to the medical device (operation 912), again ultimately activating the indicator located thereon. Operations 908 through 912 can be repeated for any number of medical devices placed in proximity to the charging device. And, as with the method of FIG. 8, updated communication signals may be sent to each medical device as any additional medical devices are brought into proximity with the charging station. The charging device may optionally receive now-and-then a status update from the associated medical devices in proximity. Therefore the associated medical devices can send repeated status signals at regular time interval or as a consequence of a communication signal being sent from the charging device. Based at least in part on the status signals received from the first and second (and additional) medical devices, a determination is made as to an action to take with regard to the various medical devices (operation 914). For example, the supervisory battery charger management system of FIG. 5 makes such a determination. Based on the determined action, an instruction is sent to the charging interface associated with the first medical device or the charging interface associated with the second medical device (operation 916). These instructions ultimately result in the charging interface (such as the type depicted in FIG. 5) transferring energy or power to the battery of one or more medical devices. In embodiments, these instructions are prioritized based on predetermined criteria.

Figure 9B:
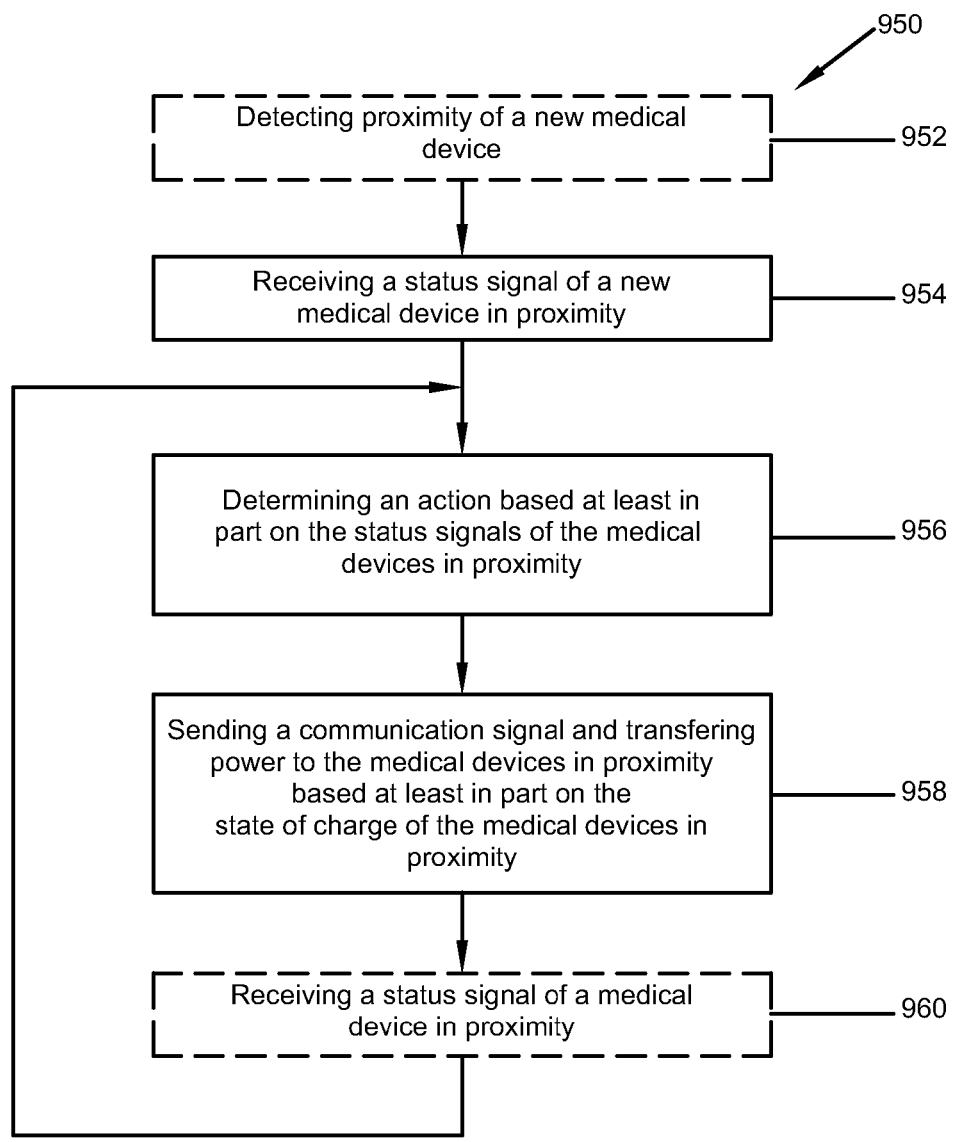
FIG. 9B is another method of managing the charging of multiple batteries of a medical device.

FIG. 9B depicts another method 950 of managing the charging of multiple batteries, typically those used in conjunction with a medical device. Similar to the methods described above, a new medical device to be charged is placed in proximity to a charging device and optionally detected (operation 952). Thereafter, the charging device receives a status signal from the new medical device (operation 954). In systems where multiple medical devices are charged, additional medical devices may also be placed in proximity with the charging device and optionally detected. Any introduction of an additional medical device, a status signal is received from the additional medical device (operation 954). The charging device determines an action based at least in part on the status signals of the medical devices in proximity (operation 956). This action is defined from the state of charge of all associated batteries and the additional instructions or preferences provided by the recipient to the charging device. The charging device sends a communication signal and transfers power to the medical devices in proximity (operation 958). In certain embodiments, power is transfer to only one of the medical device batteries, as determined by the charging device. The communication signal can include an instruction for each associated medical device to activate an indicator. The charging device may optionally receive now-and-then status updates from the associated medical devices in proximity (operation 960). Therefore the associated medical devices may send repeatedly status signals at regular time intervals or as a consequence of a communication signal emanating from the charging device. Operations 956 through 960 can be repeated for any number of medical devices placed in proximity to the charging device. Any new medical device brought in proximity causes operation 952 to start again. Based at least in part on the status signals received from the medical devices in proximity, a determination is made as to an action to take with regard to the various medical devices (operation 956). For example, the supervisory battery charger management system of FIG. 5 makes such a determination. Based on the determined action, an instruction is sent to the charging interface for each associated medical device (operation 958). These instructions ultimately result in the charging interface (such as the type depicted in FIG. 5) transferring energy or power to the battery of one or more medical devices. These instructions are prioritized based on predetermined criteria.

Many factors can be considered by the charging device to prioritize the charging of a number of batteries. In general, the charging device determines an action based at least in part on the status signals of the medical devices in proximity. This action can be based on the states of charge of all associated batteries and any additional instructions or preferences provided by the recipient to the charging device. For example, the charging device may determine which battery of the various devices can be fully recharged in the fastest time and prioritize energy transfer to that battery. To do this, the charging device checks the battery charge level of all batteries and then makes the best decision. The charging device can also equilibrate the number of charge and discharge events for each battery so each battery is optimized for lifetime. Additionally, the charging device will stop charging if a battery temperature exceeds a certain predetermined limit. This excess temperature event can occur, for example, during a fast charge scenario. If the charging device is configured to charge only a single battery at a time, once charging of one battery is stopped, the status of the remaining batteries may be reevaluated and a new action for a different battery taken. The charging device can also transfer energy based on other criteria or on recipient preferences, instructions, and/or other requirements. Alternatively or additionally, the charging device can simply charge the first medical device present, or the one with the highest present charge capacity.

For particular medical devices, for example, the exterior portions of cochlear implants, the systems and methods described herein enable a recipient to manage the charging of multiple external portions of their implant. When therapy to a cochlear implant recipient is interrupted, that recipient loses their ability to hear sounds, including sounds that warn them of danger. The systems and methods described herein enable a recipient to always have a satisfactorily charged external portion at the ready, so as to limit such an undesirable situation.

Figure 10A:
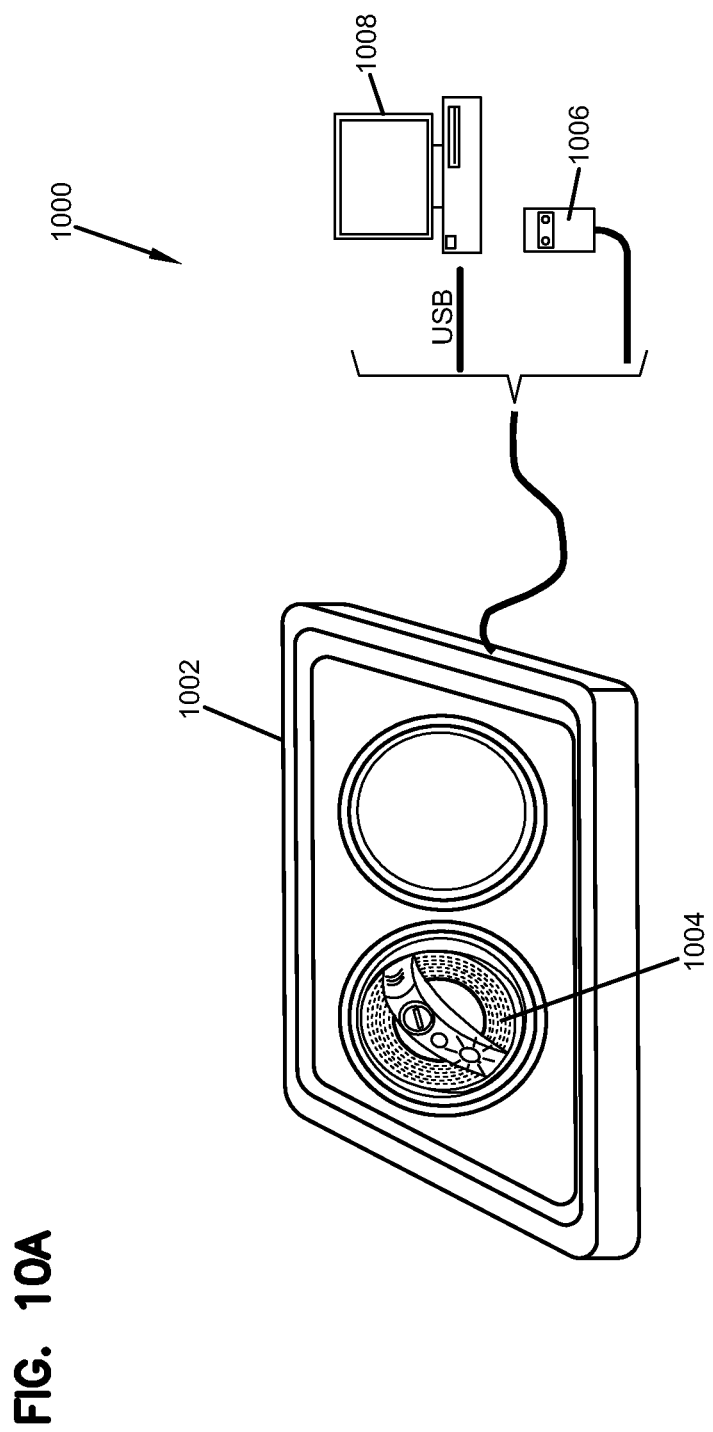
FIG. 10A is a schematic perspective view of an embodiment of a battery charging system.
Figure 10B:
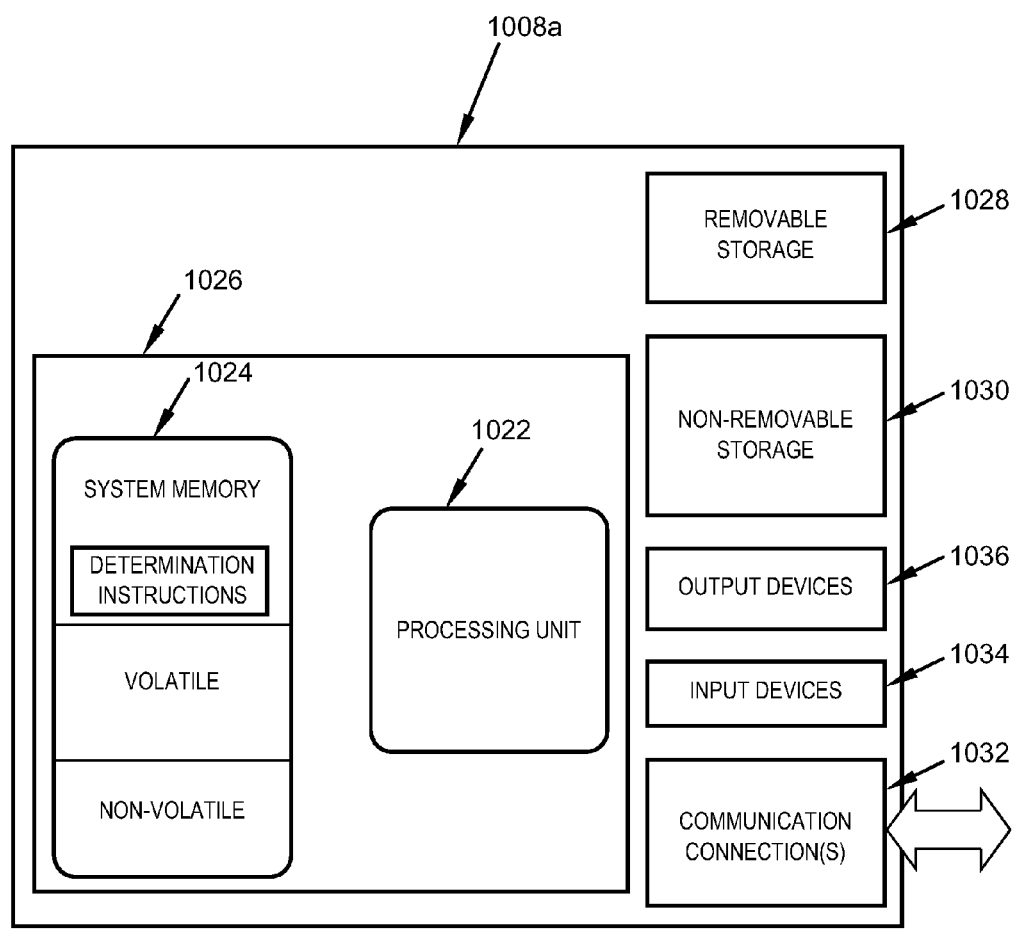
FIG. 10B illustrates one embodiment of a suitable operating environment in which one or more of the present embodiments may be implemented.

FIG. 10A depicts a schematic perspective view of an example of a system 1000 including a charging device 1002 and an external portion 1004 of an auditory prosthesis. As described above, the charging device 1004 can include all internal controls and components, thus requiring only a power plug 1006 for operation. In another embodiment, however, the charging device 1002 may include the various components depicted therein, but the operational software may be located in an operating environment of an associated computer 1008. Such a computer operating environment 1008a is depicted in FIG. 10B. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 1008a typically includes at least one processing unit 1022 and memory 1024. Depending on the exact configuration and type of computing device, memory 1024 (storing, among other things, instructions to perform the determination, prioritization, and charging methods described herein) may be volatile (such as RAM), non-volatile (such as ROM, flash memory, etc.), or some combination of the two. This most basic configuration is illustrated in FIG. 10B by line 1026. Further, environment 1008a may also include storage devices (removable, 1028, and/or non-removable, 1030) including, but not limited to, magnetic or optical disks or tape. Similarly, environment 1008a may also have input device(s) 1034 such as touch screens, keyboard, mouse, pen, voice input, etc. and/or output device(s) 1036 such as a display, speakers, printer, etc. Also included in the environment may be one or more communication connections, 1032, such as LAN, WAN, point to point, Bluetooth, RF, etc.

Operating environment 1008a typically includes at least some form of computer readable media. Computer readable media can be any available media that can be accessed by processing unit 1022 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 1008a may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

In some embodiments, the components described herein comprise such modules or instructions executable by computer system 1008a that may be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 1008a is part of a network that stores data in remote storage media for use by the computer system 1008a.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure described some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method comprising:
   receiving a first status signal from a first medical device, wherein the first medical device comprises a first battery;
   sending a first communication signal to the first medical device, wherein the first communication signal is associated with a first state of charge of the first battery;
   activating an indicator based at least in part on the first status signal; and
   transferring energy based at least in part on the first status signal.

2. The method of claim 1, further comprising:
   receiving a second status signal from a second medical device, wherein the second medical device comprises a second battery; and
   transferring energy to at least one of the first battery and the second battery based at least in part on the first status signal and the second status signal.

3. The method of claim 2, further comprising sending a second communication signal to the second medical device, wherein the second communication signal is associated with a second state of charge of the second battery.

4. The method of claim 1, wherein the transferred energy comprises at least one of a trickle charge, a normal charge, a fast charge, an end of charge, and a forced discharge.

5. The method of claim 1, wherein the first status signal comprises at least one of a level of charge, a voltage, a current, a percentage of total charge available, a battery charging history, a battery type, a battery identification number, and a battery authentication key, of the first battery.

6. The method of claim 1, wherein the indicator comprises at least one of a plurality of indication states.

7. The method of claim 2, further comprising:
   receiving a third status signal from a third medical device, wherein the third medical device comprising a battery; and
   transferring energy to at least one of the first battery, the second battery, and the third battery based at least in part on the first status signal, the second status signal, and the third status signal.

8. A method comprising:
   sending a first status signal from a first medical device to a charging device when the first medical device is located proximate the charging device, wherein the first medical device comprises a first battery and an indicator;
   receiving a first communication signal from the charging device, wherein the first communication signal is associated with a first state of charge of the first battery and instructs the first medical device to activate the indicator; and
   receiving power based at least in part on the first status signal.

9. The method of claim 8, wherein the received energy comprises at least one of a trickle charge, a normal charge, a fast charge, an end of charge, and a forced discharge.

10. The method of claim 8, wherein the first status signal comprises at least one of a level of charge, a voltage, a current, and a percentage of total charge available, of the first battery.

11. The method of claim 8, wherein the indicator comprises at least one of a plurality of indication states.

12. The method of claim 11, wherein the plurality of indication states are associated a state selected from the following: a charging state, a discharging state, a charged state, steady state, a low battery state, a high battery state, and an error state.

13. The method of claim 8, wherein the indicator comprises at least one of a speaker, an LED, a display, and a vibration element.

14. A method comprising:
   receiving a first status signal associated with a first battery of a first medical device;
   receiving a second status signal associated with a second battery of a second medical device;
   determining an action based at least in part on the first status signal and the second status signal; and
   sending an instruction to transfer energy to only one of the first battery and the second battery based at least in part on the determined action.

15. The method of claim 14, further comprising sending a first communication signal to the first medical device, wherein the first communication signal is associated with a first state of charge of the first battery.

16. The method of claim 15, further comprising sending a second communication signal to the second medical device, wherein the second communication signal is associated with a second state of charge of the second battery.

17. The method of claim 14, wherein the instruction comprises instruction to transfer energy as a trickle charge, a normal charge, a fast charge, an end of charge, and a forced discharge.

18. The method of claim 15, wherein the first medical device further comprises an indicator and wherein the first communication signal causes the indicator to activate.

19. The method of claim 18, wherein the indicator comprises at least one of a plurality of indication states.

20. The method of claim 14, further comprising transferring energy to at least one of the first battery and the second battery.

21. The method of claim 14, wherein the first status signal and the second status signal are received from an output of the charging device at a device external to each of the charging station, the first medical device, and the second medical device.

22. The method of claim 21, wherein the determining step is performed by the external device, wherein the external device is a personal computer.

23. The method of claim 14, wherein the action is determined based at least in part on a recipient instruction.

24. A system comprising:
   a first medical device comprising a first battery;
   a charging device for receiving the first medical device; and
   a processor coupled to the charging device, wherein the processor is capable of executing instructions that, when executed, perform a method comprising:
      receiving a first status signal from the first medical device; and
      sending a first communication signal to the first medical device, wherein the first communication signal is associated with a first state of charge of the first battery.

25. The system of claim 24, further comprising a second medical device comprising a second battery, and wherein at least one of the first medical device and the second medical device comprise an external portion of a cochlear implant.

26. The system of claim 25, wherein the method further comprises:
   receiving a second status signal from the second medical device;
   determining an action based at least in part on the first status signal; and
   sending an instruction to transfer energy to at least one of the first battery and the second battery based at least in part on the determined action.

27. The system of claim 25, wherein the method further comprises sending a second communication signal to the second medical device, wherein the second communication signal is associated with a second state of charge of the second battery.

28. The system of claim 25, further comprising a third medical device comprising a third battery.

29. The system of claim 28, wherein the method further comprises:
   receiving a third status signal from a third medical device;
   determining an action based at least in part on the first status signal, the second status signal, and the third status signal; and
   sending an instruction to transfer energy to at least one of the first battery, the second battery, and the third battery based at least in part on the determined action.

30. The system of claim 26, wherein the method further comprises transferring energy to at least one of the first battery and the second battery.

* * * * *